United States Patent
Park et al.

(10) Patent No.: US 9,758,458 B2
(45) Date of Patent: *Sep. 12, 2017

(54) METHOD FOR PURIFYING ISOPROPYL ALCOHOL

(71) Applicant: LG CHEM, LTD., Seoul (KR)

(72) Inventors: Jong Suh Park, Daejeon (KR); Sung Kyu Lee, Daejeon (KR); Joon Ho Shin, Daejeon (KR); Jong Ku Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/912,835

(22) PCT Filed: Aug. 20, 2014

(86) PCT No.: PCT/KR2014/007736
§ 371 (c)(1),
(2) Date: Feb. 18, 2016

(87) PCT Pub. No.: WO2015/026160
PCT Pub. Date: Feb. 26, 2015

(65) Prior Publication Data
US 2016/0207858 A1    Jul. 21, 2016

(30) Foreign Application Priority Data

Aug. 20, 2013 (KR) .................. 10-2013-0098665
Aug. 20, 2014 (KR) .................. 10-2014-0108602

(51) Int. Cl.
*C07C 29/76* (2006.01)
*C07C 29/80* (2006.01)
(Continued)

(52) U.S. Cl.
CPC .............. *C07C 29/76* (2013.01); *B01D 3/141* (2013.01); *B01D 3/145* (2013.01); *B01D 61/362* (2013.01);
(Continued)

(58) Field of Classification Search
CPC ......... C07C 29/76; C07C 29/80; C07C 31/10; C07B 63/00
See application file for complete search history.

(56) References Cited

U.S. PATENT DOCUMENTS

| | | | |
|---|---|---|---|
| 5,868,906 A * | 2/1999 | Adams | B01D 3/146 210/640 |
| 7,799,958 B2 * | 9/2010 | Bonmann | C07C 37/08 568/798 |
| 2011/0303526 A1 * | 12/2011 | Lee | B01D 3/14 203/81 |

FOREIGN PATENT DOCUMENTS

| | | |
|---|---|---|
| JP | 11-506431 A | 6/1999 |
| KR | 10-1997-0006256 A | 2/1997 |

(Continued)

OTHER PUBLICATIONS

"ChemicalEngineering Handbook," Japan, Maruzen Publishing Co. Ltd., 2011, Revised edition 7, pp. 426-428 (with English translation).

*Primary Examiner* — Medhanit Bahta
(74) *Attorney, Agent, or Firm* — Dentons US LLP (57) ABSTRACT

Provided are a method of and a device for purifying isopropyl alcohol. Water may be effectively removed from a feed including water and isopropyl alcohol while consuming a minimum amount of energy, and therefore, a high-purity isopropyl alcohol may be obtained.

9 Claims, 3 Drawing Sheets (51) Int. Cl.
    *B01D 61/36*    (2006.01)
    *B01D 3/14*    (2006.01)

(52) U.S. Cl.
    CPC ...... *C07C 29/80* (2013.01); *B01D 2311/2669* (2013.01)

(56) References Cited

FOREIGN PATENT DOCUMENTS

| | | |
|---|---|---|
| KR | 10-1999-0014837 A | 2/1999 |
| KR | 10-2003-0007838 A | 1/2003 |
| KR | 10-2004-0085710 A | 10/2004 |
| KR | 10-2009-0031633 A | 3/2009 |
| KR | 10-2010-0084311 A | 7/2010 |

\* cited by examiner

METHOD FOR PURIFYING ISOPROPYL ALCOHOL

This application is a National Phase entry of PCT/KR2014/007736, filed on Aug. 20, 2014 and claims priority to Korean Application Nos. 10-2014-0108602, filed Aug. 20, 2014 and 10-2013-0098665, filed Aug. 20, 2013, all of which are incorporated by reference for all purposes as if fully set forth herein.

TECHNICAL FIELD

The present invention relates to a method of and a device for purifying isopropyl alcohol.

BACKGROUND ART

Isopropyl alcohol (IPA) is used in various applications, for example, as a cleaning agent in the electronics industry to manufacture semiconductors or liquid crystal displays (LCDs).

IPA may be prepared using propylene or acetone. In most cases, in the process of preparing IPA, an IPA reaction product including a large amount of water is obtained, and the reaction product forms an azeotrope including water. That is, water having a boiling point of approximately 100° C. and IPA having a boiling point of 82.5° C. at a normal pressure form a common ratio of IPA of 87.9 wt % at a temperature of 80.4° C., and thus high-purity IPA should be efficiently prepared by removing water from the feed, and a large amount of energy is consumed to remove the water in a simple distillation process. As a method of obtaining high-purity IPA from the azeotrope, a distillation method of adding an azeotropic agent, which is a material for forming an extract or azeotrope, is known.

DISCLOSURE

Technical Problem

The present invention is directed to providing a method of and a device for purifying IPA.

Technical Solution

Figure 1:
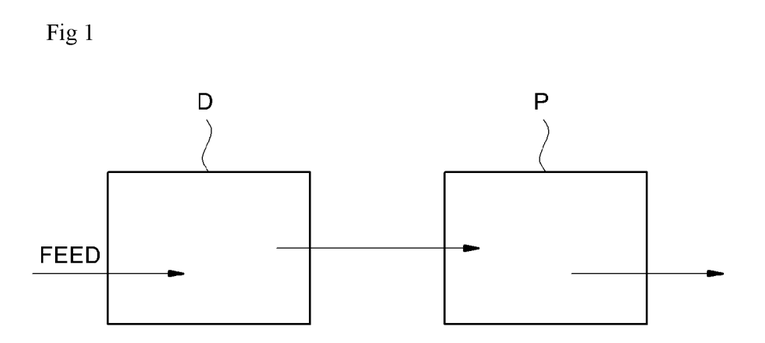
FIG. 1 shows a process of the above-described method.

In one aspect, a method of purifying IPA is provided. An exemplary purifying method includes, as shown in FIG. 1, removing water by providing a feed to a dehydration means (D) (hereinafter referred to as a "dehydration process"), purifying the feed by removing water via the dehydration means (D) and introducing the feed into a purification means (P) (hereinafter referred to as a "purification process"). According to the purification method of the present invention, in the process of purifying IPA using the dehydration means (D) and a divided wall column (DWC) 200, optimal operating conditions for the DWC to minimize a water content in an IPA product may be deduced, thereby purifying IPA to a high purity. In addition, IPA may be purified with high efficiency using one DWC, compared to when using a purification means (P) in which two general columns are connected.

Here, the term "removal of water" does not refer to 100% removal of water included in a feed, but refers to forming a rich flow having a high IPA content by providing the feed to the dehydration means (D), and removing water or performing a purification process. The term "rich flow" used herein may refer to a flow having a higher IPA content included in the flow passing through the dehydration means (D) or the purification means (P) than the content of IPA included in the feed before being provided to the dehydration means (D), and for example, a flow including IPA included in the flow passing through the dehydration means (D) or the purification means (P) at a content of 50 wt % or more, 80 wt % or more, 90 wt % or more, 95 wt % or more, or 99 wt % or more.

In one example, the feed provided to the dehydration means (D) in the dehydration process may include IPA and water. A water content of the feed, that is, a content of water in the feed, may be 5,000 ppm or less, for example, 3,000 ppm or less, 2,500 ppm or less, or 2,200 ppm or less. In addition, the lower limit of the water content in the feed may be, for example, 1,200 ppm. The water content in the feed may serve as a very important factor for efficiency, and thus the water content of the feed is necessarily adjusted within the above range. A particular composition of the feed is not particularly limited as long as it includes IPA and water, and a water content is adjusted within the above range. Conventionally, depending on a method of preparing a feed including IPA, the feed may include various types of impurities, which may be efficiently removed by the above method.

In this method, the dehydration means (D) into which the feed is introduced may be a membrane system. The dehydration means (D) including the membrane system 100 may be installed to discharge the feed having a decreased water content from 3,000 ppm to 1,200 ppm or less, for example, 1,000 ppm or less, 700 ppm or less, 500 ppm or less, or 300 ppm or less through the dehydration process. Accordingly, the dehydration process may include removing water from the feed provided to the dehydration means (D) to adjust a water content of the feed to 1,200 ppm or less, for example, 1,000 ppm or less, 700 ppm or less, 500 ppm or less, or 300 ppm or less. When the water content is adjusted within the above range through the dehydration means (D), efficiency of a subsequent purification process may be increased. The term "membrane system" used herein means a system or device for separating a liquid using a separation film.

As the membrane system 100 of the dehydration means (D), any system using a separation film, for example, a pervaporation system or a vapor permeation system, may be used without particular limitation.

The term "pervaporation" used herein means a method for increasing purity of the feed by providing a liquid feed to a pervaporation film and selectively permeating a material having an affinity to the film, and the material passing through the pervaporation film is discharged by evaporation in a constant vacuum state, and captured by being cooled in a cooler. The pervaporation system may be applied to the purification method of the present invention when the feed is in a liquid state. When the dehydration process is performed using the pervaporation system, before the DWC 200 is charged with the feed, water is selectively removed in the dehydration process, thereby economically yielding high-purity IPA, compared to when water is removed by a simple distillation process.

In one example, when the dehydration means (D) includes the pervaporation system, in the dehydration process, the introduction of the liquid feed into the pervaporation system during the dehydration process may be performed at a temperature of, for example, 40 to 120° C., 70 to 110° C., or 80 to 100° C., but the present invention is not particularly limited thereto. In addition, the introduction of the liquid feed into the pervaporation system may be performed under a pressure of, for example, 1.0 to 10.0 kg/cm$^2$, 2.0 to 8.0 kg/cm$^2$, 2.5 to 6.0 kg/cm$^2$, or 3.0 to 5.0 kg/cm$^2$. The dehydration process of the liquid feed may be efficiently performed in the range of the above-described temperature and/or pressure. However, the range of the temperature and/or pressure may be suitably changed in consideration of a desired dehydration amount and the separation film used. For example, generally, as the temperature and the pressure are increased, permeability of the separation film may be increased, but the upper limits of the temperature and the pressure may be changed according to a type of the separation film and process conditions. In addition, as the temperature and the pressure are increased, a permeation rate and a permeation amount may be increased, but the upper limits may be adjusted within suitable ranges according to a type of the material for the separation film used herein and durability of the separation film.

The term "vapor permeation" refers to a film separation method for separating a desired gas through a separation film by evaporating a feed to bring the gas in contact with the separation film. In the purification method, when the feed is in a gaseous state, the vapor permeation may be preferably applied. When a dehydration process is performed using the vapor permeation system, an azeotropic point is not generated, and thus water may be more efficiently removed than when the dehydration process is performed by distillation, and therefore high-purity IPA may be economically obtained.

In one example, the feed introduced into the vapor permeation system of the dehydration means (D) may be introduced into the vapor permeation system at a temperature of a boiling point or more of a mixed composition of water and IPA. The introduction of a gas-phase feed into the vapor permeation system in the dehydration process may be performed at, for example, 90° C. or more, 100° C. or more, 110° C. or more, 120° C. or more, or 150° C. or more, and the upper limit of the temperature at which the gas-phase feed is introduced may be changed according to thermal or chemical characteristics of the separation film used, and may be, but is not particularly limited to, for example, approximately 180° C. In addition, the introduction of the gas-phase feed into the vapor permeation system may be performed under a pressure of, for example, 1.0 to 10.0 $kg/cm^2$, 2.0 to 8.0 $kg/cm^2$, or 3.0 to 6.0 $kg/cm^2$. In the above-described temperature and/or pressure ranges, a process of dehydrating a gas-phase feed may be efficiently performed. However, the temperature and/or pressure ranges may be suitably changed in consideration of a desired dehydration amount and the type of the separation film used.

The separation film which can be used in the pervaporation system or vapor permeation system may be an organic separation film such as a polymer membrane, an inorganic separation film, or an organic/inorganic separation film manufactured by mixing an organic material and an inorganic material according to the type of material used, and for the dehydration means (D) of the present invention, various separation films known in the art may be used according to a desired separated component. For example, as the hydrophilic separation film, a separation film formed of a silica gel, a separation film formed of a polymer such as PVA or polyimide, or a zeolite separation film may be used, but these may be suitably changed in consideration of a desired dehydration amount and a composition of the feed. As the zeolite separation film, a zeolite film produced by Pervatech, a zeolite A separation film produced by i3nanotec, or a zeolite NaA separation film may be used, but the present invention is not limited thereto.

In addition, the pervaporation system or the vapor permeation system may include a vacuum device. The vacuum device is a device for forming a vacuum to allow a separable component of the feed in contact with the separation film to be easily separated from the film, and may be a device composed of a vacuum storage tank and a vacuum pump.

In the exemplary dehydration means (D), the columns 110 and 111 charged with an adsorbent may be included in addition to the membrane system 100. For example, when the feed having a water content adjusted to 1,200 ppm or less is introduced through the above-described membrane system 100, the column charged with an adsorbent may be equipped to discharge the feed by adjusting the water content in the feed to 50 to 500 ppm, for example, 100 to 500 or 150 to 500 ppm, through the second dehydration process. When the water content is adjusted within the above range using the columns 110 and 111, efficiency of the subsequent purification process may be increased.

In one example, as the adsorbent, various adsorbents known in the art including a molecular sieve, a silica gel, activated alumina, activated carbon, and an ion exchange resin may be used, but the present invention is not limited thereto.

For example, as the molecular sieve of the dehydration means (D), a known molecular sieve may be used without particular limitation as long as it is installed to have the dehydration capability as described above. For example, as the molecular sieve, a zeolite-based molecular sieve, a silica-based molecular sieve, an alumina-based molecular sieve, a silica-alumina-based molecular sieve, or a silicate-alumina-based molecular sieve may be used.

As the molecular sieve, for example, a molecular sieve having an average micropore size of approximately 1.0 to 5.0 Å or 2.0 to 4.0 Å may be used. In addition, a specific surface area of the molecular sieve may be, for example, approximately 100 to 1,500 $m^3/g$. The dehydration capability of the dehydration means (D) may be suitably adjusted using the molecular sieve having the micropore size and specific surface area in the above ranges.

In one example, the dehydration means (D) may include, for example, at least two columns 110 and 111 charged with the molecular sieve. When the dehydration means (D) includes at least two columns and a method of alternately providing the feed to the plural columns is employed, the efficiency of the process may be further increased.

The method may further include regenerating the molecular sieve by detaching water adsorbed to the molecular sieve during dehydration. The detachment process of the molecular sieve may be performed in the purification process after the dehydration process, and when the plurality of columns 110 and 111 are used as described above, while the dehydration process is performed in one column, the detachment process of the molecular sieve may be performed in the other column.

The regeneration may be performed using argon, carbon dioxide, or nitrogen, or a low alkane such as methane, ethane, propane, or butane. In one example, the regeneration process may be performed using nitrogen gas. When nitrogen gas is used, the regeneration process may be performed at a temperature of approximately 175 to 320° C. or 180 to 310° C. In addition, an amount of the nitrogen gas provided for detachment may be adjusted to, for example, approximately 1,100 to 1,500 $Nm^3/hr$. In the above range, the regeneration or detachment process may be efficiently performed. However, the temperature and flow rate may be changed according to a specific type or amount of the molecular sieve used herein.

A purification process may be performed by providing the feed in which a water content is adjusted to 1,200 ppm or less through the dehydration process to a purification means (P). In one example, the purification means (P) may be a DWC.

Figure 2:
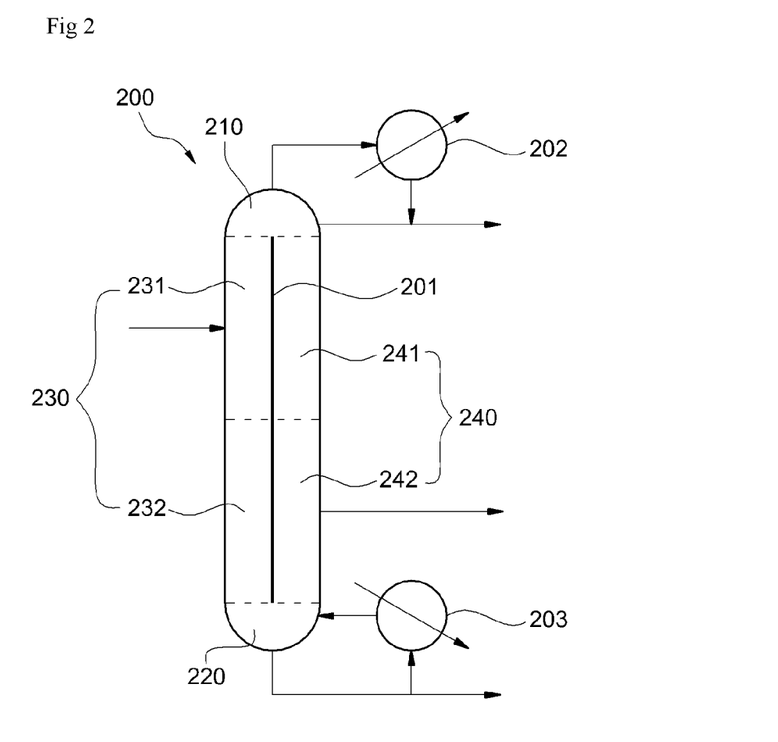
FIG. 2 shows a dehydration means used in the method.

Here, the DWC 200 is a device designed to distill a feed including three components, for example, having a low boiling point, a middle boiling point, and a high boiling point. The DWC 200 is a device similar to a thermally coupled distillation column (Petlyuk column) in terms of a thermodynamic aspect. The thermally coupled distillation column has a structure in which a pre-separator and a main separator are thermally integrated. The column is designed to primarily separate low-boiling-point and high-boiling-point materials from the preliminary separator, and charge each of top and bottom parts of the pre-separator to a supply plate of the main separator and separate low-boiling-point, medium-boiling-point, and high-boiling-point materials from the main separator. On the other hand, the DWC 200 is formed by installing a dividing wall 201 in the column and integrating a pre-separator into a main separator.

The DWC 200 may have the structure as shown in FIG. 2. FIG. 2 shows an exemplary DWC 200. As shown in FIG. 2, the exemplary column may have a structure which is divided by the dividing wall 201, and includes a condenser 202 disposed in an upper portion and a reboiler 203 in a lower portion. In addition, as virtually divided by a dotted line in FIG. 2, the DWC 200 may be divided into, for example, a top region 210 discharging a low-boiling-point flow, a bottom region 220 discharging a high-boiling-point flow, a feed inflow region 230 into which the feed is introduced, and a product outflow region 240 discharging a product. The feed inflow region 230 may include an upper inflow region 231 and a lower inflow region 232, and the product outflow region 240 may include an upper product outflow region 241 and a lower product outflow region 242. Here, the term "upper and lower inflow regions" may refer to upper and lower regions, respectively, created when a feed-providing part of a space divided by the dividing wall 201 in the structure of the DWC 200, that is, the feed inflow region 230, is divided into equal two parts in a length direction of the column. In addition, the term "upper and lower product outflow regions" may refer to upper and lower regions created when a space of a product releasing side, which is divided by the dividing wall 201 in the DWC 200, that is, the product outflow region 240, is divided into equal two parts in a length direction of the column. The term "low-boiling-point flow" refers to a flow in which relatively low-boiling-point components are rich among the feed flows including three components such as low-, middle-, and high-boiling-point components, and the term "high-boiling-point flow" refers to a flow in which relatively high-boiling-point components are rich among the feed flows including three of low-, medium-, and high-boiling-point components.

In the purification method of the present invention, the feed introduced into the feed inflow region 230 of the DWC 200 is purified in the DWC 200. In addition, the component having a relatively low boiling point in the feed introduced into the feed inflow region 230 is transferred to the top region 210, and the component having a relatively high boiling point is transferred to the bottom region 220. A component having a relatively low boiling point in the component transferred to the bottom region 220 is transferred to the product outflow region 240 and discharged as a product flow, or transferred to the top region 210. In addition, a component having a relatively high boiling point in the component transferred to the bottom region 220 is discharged from the bottom region 220 as a high-boiling-point flow. A part of the high-boiling-point flow discharged from the bottom region 220 may be discharged as a flow of the high-boiling-point component, and the rest may be heated in a reboiler 203 and then reintroduced into the bottom region 220 of the DWC 200. Meanwhile, from the top region 210, a flow of the low-boiling-point component having a very high water content may be discharged, the flow discharged from the top region 210 may be condensed in a condenser 202, a part of the condensed flow may be discharged, and the rest may be reintroduced into the top region 210 of the DWC 200. In addition, the flow reintroduced into the top region 210 may be purified again in the DWC 200, thereby minimizing a content of IPA discharged from the top region 210 and maximizing a water content discharged from the top region 210.

A specific type of the DWC 200 that can be used in the purification method is not particularly limited. For example, the DWC having a general structure as shown in FIG. 2 is used, or a column modified in position or shape of a divided wall in the column in consideration of purification efficiency may also be used. In addition, the number of plates and an inner diameter of the column are not particularly limited either, and may be determined based on, for example, the number of theoretical plates calculated from a distillation curve considering the composition of the feed.

In this method, the DWC 200 performing the purification process may be installed to discharge the feed having a water content adjusted to 1,200 ppm or less by reducing the water content of the feed to 150 ppm or less, for example, 120 ppm or less, 110 ppm or less, 100 ppm or less, 80 ppm or less, 60 ppm or less, 50 ppm or less, 30 ppm or less, or 10 ppm or less, through the purification process. Accordingly, in the purification process, water may be removed from the feed provided to the DWC 200 to adjust the water content of the feed to 150 ppm or less, for example, 120 ppm or less, 110 ppm or less, 100 ppm or less, 80 ppm or less, 60 ppm or less, 50 ppm or less, 30 ppm or less, or 10 ppm or less. According to the DWC 200, the water content may be adjusted within the above range, and IPA may be purified at a high purity at the same time.

The DWC 200 may be installed to provide, for example, the feed passing through the membrane system 100 to the feed inflow region 230 of the column. Accordingly, in the purification process, the feed in which the water content of the feed passing through the dehydration process is adjusted to 1,200 ppm or less may be provided to the feed inflow region 230 of the column. When the feed is provided to the DWC 200, in consideration of the composition of the feed, for example, as shown in FIG. 2, if the feed is provided to the upper supply region 231, efficient purification can be performed.

Accordingly, the DWC 200 may be installed to discharge a product including the purified IPA and having a water content of 150 ppm or less from a lower product outflow region 242, preferably, a middle part of the lower product outflow region 242. That is, the purification method may include yielding the product including the purified IPA and having a water content of 150 ppm or less from 50 to 90%, 55 to 80%, or 60 to 75% of plates of the number of theoretical plates calculated from the lower product outflow region 242, preferably, a top of the DWC 200. For example, when the number of theoretical plates of the DWC 200 is 100 plates, the product having a water content of 150 ppm or less may be discharged from 50 to 90 or 60 to 75 plates, and efficiency of the purification process may be further increased by adjusting a discharging location of the product as described above. The term "middle part of the lower product outflow region" used herein means a site at which the lower product outflow region 242 is divided into two equal parts in a length direction of the DWC 200.

The number of theoretical plates of the DWC 200 required to adjust a water content of the feed in which the water content is adjusted to 1,200 ppm or less as described above to be 150 ppm or less may be, but is not limited to, 70 to 120 plates, 80 to 110 plates, or 85 to 100 plates, and may be suitably changed according to a flow amount of an introduced feed and a process condition.

Meanwhile, due to a structural characteristic of the DWC 200 in which an internal circulation flow rate may not be adjusted once a design is determined, unlike a Petlyuk column, flexibility according to a change in operating conditions is decreased, and a variety of accurate copies of disturbance and determination of an easily controllable control structure are required in an early stage of designing the column. Moreover, a designed column structure and operating conditions of the DWC including a location of a supply plate, determination of sections of the dividing wall, a location of a plate for producing a middle-boiling-point material, the total number of theoretical plates, a distillation temperature, and a distillation pressure are very limited, and a design structure including the number of plates of the column, and locations of a supply plate and a releasing plate, and operating conditions including a distillation temperature, a pressure, and a reflux ratio should be specially changed according to characteristics of a compound to be distilled. In the purification method of the present invention, as described above, an operating condition of the DWC 200 suitably designed to purify IPA may be provided to save energy and reduce a cost of equipment.

In one example, as described above, when the feed in which a water content is adjusted to 1,200 ppm or less is introduced into the DWC 200, and the water content in the feed is adjusted to 150 ppm or less in the DWC 200 through the purification process, the reflux ratio of the top region 210 of the DWC 200 may be adjusted in a range of 30 to 70, for example, 40 to 60 or 45 to 60. For example, as the water content in the feed introduced into the DWC 200 is high, it is necessary to considerably adjust the reflux ratio of the top region 210 for removing water in the feed and obtaining high-purity IPA. However, in the purification method of the present invention, the water content in IPA introduced to the DWC 200 is adjusted to 1,200 ppm or less, and the reflux ratio of the top region 210 into the DWC 200 is adjusted within a specific range as described above, thereby highly reducing a water content in IPA obtained from the lower product outflow region 242.

The feed may be provided to the DWC 200 at a flow rate of, for example, approximately 5,000 to 13,000 kg/hr. In addition, a temperature of the provided feed may be adjusted to be, for example, approximately 50 to 135° C., 60 to 110° C., or 80 to 100° C. When the feed is provided at the above-described flow rate and temperature, suitable distillation efficiency may be achieved.

As described above, during the distillation performed by providing the feed in which a water content is adjusted to 1,200 ppm or less to the DWC 200, the operating temperature of the top region 210 of the DWC 200 may be adjusted to 40 to 120° C., for example, approximately 45 to 110° C., 50 to 105° C., 55 to 100° C., or 60 to 100° C. In this case, the operating pressure of the top region 210 of the DWC 200 may be adjusted to 0.1 to 10.0 kg/cm$^2$, for example, approximately 0.2 to 5.5 kg/cm$^2$, 0.3 to 4.5 kg/cm$^2$, 0.6 to 4.0 kg/cm$^2$, 0.8 to 3.5 kg/cm$^2$ or 0.82 to 3.2 kg/cm$^2$. At such operating temperature and pressure, efficient distillation according to the composition of the feed may be performed.

In the specification, the pressure is, unless particularly defined otherwise, an absolute pressure.

The operating and pressure conditions in the DWC 200 may be changed according to the temperature and pressure conditions of the top region 210. In one example, when the temperature of the top region 210 of the DWC 200 is adjusted to 40 to 120° C., a temperature of release flow discharged from the lower product outflow region 242 of the DWC 200 may be adjusted to 60 to 130° C., for example, approximately 70 to 120° C., 75 to 115° C., or 78 to 115° C. In addition, when the pressure of the top region 210 of the DWC 200 is adjusted to 0.2 to 5.5 kg/cm$^2$, the operating pressure of the lower product outflow region 242 of the DWC 200 may be adjusted to 0.3 to 6.0 kg/cm$^2$, for example, approximately 0.8 to 3.8 kg/cm$^2$, 0.9 to 3.5 kg/cm$^2$, 0.95 to 3.3 kg/cm$^2$ or 0.98 to 3.27 kg/cm$^2$. With such operating temperature and pressure, efficient distillation according to a composition of the feed can be performed.

In addition, when the temperature of the top region 210 of the DWC 200 is adjusted to 40 to 120° C., the operating temperature of the bottom region 220 of the DWC 200 may be adjusted to 80 to 160° C., for example, approximately 90 to 150° C., 95 to 140° C., or 98 to 138° C. In addition, when the pressure of the top region 210 of the DWC 200 is adjusted to 0.2 to 5.5 kg/cm$^2$, the operating pressure of the bottom region 220 of the DWC 200 may be adjusted to 0.3 to 6.0 kg/cm$^2$, for example, approximately 0.8 to 4.0 kg/cm$^2$, 1.0 to 3.5 kg/cm$^2$, or 1.05 to 3.4 kg/cm$^2$. At such operating temperature and pressure, efficient distillation according to the composition of the feed can be performed.

Here, the operating condition of the DWC 200 may be further adjusted when needed in consideration of purification efficiency.

Other conditions of the DWC 200 on which the purification process is performed, for example, the number of plates or inner diameter of each column are not particularly limited. For example, the number of theoretical plates of the DWC 200 may be determined based on the number of theoretical plates calculated by a distillation curve of the feed. In addition, flow rates of the upper and lower discharged products from the DWC 200 may be determined to achieve, for example, the above-described operating pressure and temperature.

In another aspect, a device for purifying IPA is provided. The exemplary purification device may be a device to be applied to the above-described purification method.

Accordingly, for example, when the above-described feed is provided, the purification device may include a dehydration means (D) installed to discharge the feed by reducing a water content to be 1,200 ppm or less, and a purification means (P) into which the feed passing through the dehydration means (D) is introduced to perform a purification process.

Specific descriptions related to the purification device may be the same as or similar to, for example, those described above.

For example, the dehydration means (D) may be a membrane system 100. As the membrane system 100 of the dehydration means (D), any system using a separation film, for example, a pervaporation system or a vapor permeation system may be used without particular limitation.

As described above, the separation film which can be used in the pervaporation system or the vapor permeation system may be an organic separation film such as a polymer membrane, an inorganic separation film, or an organic/inorganic separation film manufactured by mixing an organic material with an inorganic material according to a type of material used, and in the dehydration means (D) of the present invention, various separation films known in the art may be used in a variety of applications according to a desired separated component. For example, as a hydrophilic separation film, a separation film formed of a silica gel, a separation film formed of a polymer such as PVA or polyimide, or a zeolite separation film may be used, but these may be suitably changed in consideration of a desired dehydration rate and the composition of the feed. For example, as the zeolite separation film, a zeolite film manufactured by Pervatech, a zeolite A separation film manufactured by i3nanotec, or a zeolite NaA separation film may be used, but the present invention is not limited thereto.

In addition, the pervaporation system or vapor permeation system may include a vacuum device. The vacuum device is a device for forming a vacuum to easily separate a component of the feed to be separated from a film after coming in contact with the separation film, for example, a device composed of a vacuum storage tank and a vacuum pump.

In the exemplary dehydration means (D), a column charged with an adsorbent may be further included in addition to the membrane system 100.

In one example, as the adsorbent, various adsorbents known in the art including a molecular sieve, a silica gel, activated alumina, activated carbon, or an ion exchange resin may be used, but the present invention is not limited thereto.

For example, as the molecular sieve of the dehydration means D, a known molecular sieve may be used without particular limitation as long as it is installed to have a dehydrating ability as described above. For example, as the molecular sieve, a zeolite-based molecular sieve, a silica-based sieve, an alumina-based sieve, a silica-alumina-based sieve, or a silicate-alumina-based sieve may be used.

As the molecular sieve, for example, a molecular sieve having an average micropore size of approximately 1.0 to 5.0 Å or 2.0 to 4.0 Å may be used. In addition, a specific surface area of the molecular sieve may be, for example, approximately 100 to 1,500 m$^3$/g. The dehydration ability of the dehydration means (D) may be suitably adjusted by using the molecular sieve having a micropore size and a specific surface area in the above ranges.

In one example, the dehydration means (D) may include at least two columns charged with a molecular sieve.

The purification device may include, for example, a purification means (P) in which the feed passing through the dehydration means (D) is introduced and subjected to a purification process, and the purification means (P) may be a DWC.

Here, the DWC 200 may be installed such that, for example, the feed passing through the dehydration means (D) is provided to a feed inflow region 230, for example, an upper inflow region 231 of the DWC 200. In addition, the DWC 200 may be installed such that the product including IPA is discharged from a lower product outflow region 242, preferably, a middle part of the lower product outflow region 242.

Specific descriptions related to the DWC 200 are the same as those described in the above-described purification method, and thus will be omitted.

Advantageous Effects

According to the present invention, high-purity IPA can be obtained from a feed including water and IPA while consuming a minimum amount of energy.

MODE FOR INVENTION

Hereinafter, the present invention will be described in further detail with reference to Examples and Comparative Examples, but the scopes of the method and device are not limited to the following Examples.

Example 1

Figure 3:
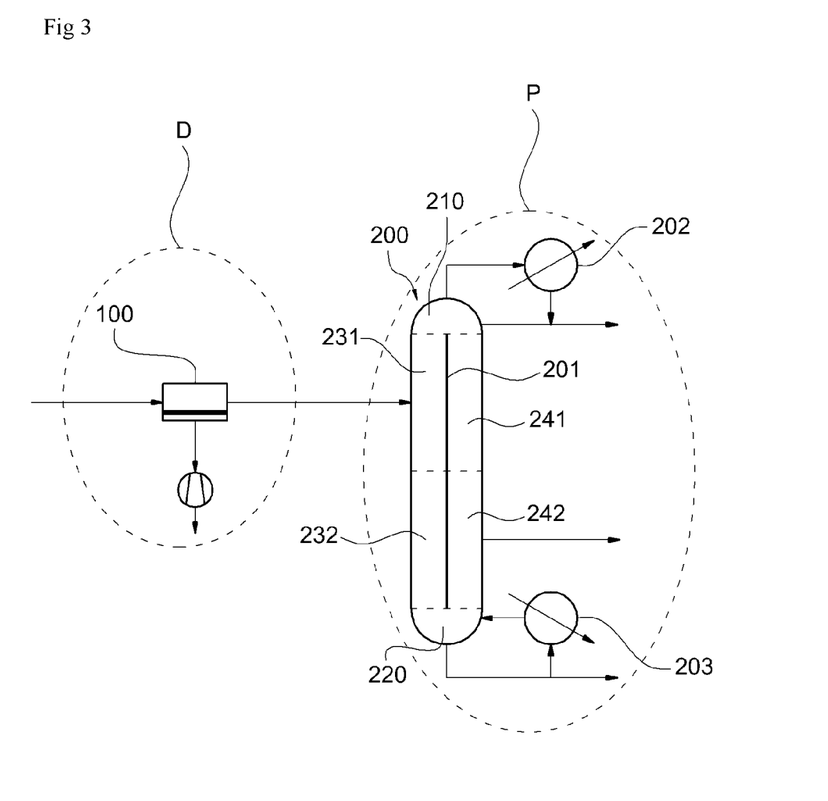
FIG. 3 shows a purification device according to a first example of the present invention.

Isopropyl alcohol (IPA) was purified using a membrane system and a divided wall column (DWC) connected with the membrane system as shown in FIG. 3. Particularly, as the dehydration means, a pervaporation system including a membrane device (HybSi membrane, Pervatech corporation) and a vacuum device was used. As a feed, a liquid feed including 98.6 wt % of IPA, approximately 3,000 ppm of water and approximately 1.1 wt % of other impurities was used. A dehydration process was performed by providing the above-described feed to the membrane system at 90° C. and adjusting a water content of the feed to approximately 1,000 ppm. Afterwards, purification was performed by introducing the feed having a water content of approximately 1,000 ppm, which went through the dehydration process, into a feed inflow region of the DWC, particularly, 20 plates of the DWC having the number of theoretical plates of 90 plates calculated based on a top, and a product material including the IPA was obtained from 60 plates of the DWC having the number of theoretical plates of 90 plates calculated based on the top.

Here, the reflux ratio of a top region of the DWC was adjusted to 57, and operating temperature and pressure of the top region were adjusted to approximately 71° C. and 1.1 kg/cm$^2$, respectively. In this case, operating temperature and pressure of a lower product outflow region were approximately 98° C. and 1.34 kg/cm$^2$, respectively, and operating temperature and pressure of the bottom region were approximately 109° C. and 1.37 kg/cm$^2$, respectively.

In this case, a content of a high boiling point component in the IPA obtained from the lower product outflow region was detected at approximately 32 ppm.

Example 2

Purification was performed by the same method as described in Example 1, except that a reflux ratio of the top region was adjusted to 54.

Example 3

Purification was performed by the same method as described in Example 1, except that a reflux ratio of the top region was adjusted to 46.

Example 4

Purification was performed by the same method as described in Example 1, except that a product including IPA was obtained from 45 plates of the DWC having the number of theoretical plates of 90 plates.

Example 5

Purification was performed by the same method as described in Example 1, except that a product including IPA was obtained from 70 plates of the DWC having the number of theoretical plates of 90 plates.

In this case, a content of a high boiling point component in IPA obtained from the lower product outflow region was detected at approximately 40 ppm.

Example 6

Purification was performed by the same method as described in Example 1, except that operating temperature and pressure of a top region were adjusted to approximately 60° C. and 0.82 kg/cm$^2$, respectively.

In this case, operating temperature and pressure of a lower product outflow region were approximately 78° C. and 0.98 kg/cm$^2$, respectively, and operating temperature and pressure of the bottom region were approximately 98° C. and 1.05 kg/cm$^2$, respectively.

Example 7

Purification was performed by the same method as described in Example 1, except that operating temperature and pressure of a top region were adjusted to approximately 100° C. and 3.2 kg/cm$^2$, respectively, and a reflux ratio was applied to maintain a water content in IPA finally obtained to be 100 ppm.

In this case, operating temperature and pressure of a lower product outflow region were approximately 115° C. and 3.27 kg/cm$^2$, respectively, and operating temperature and pressure of a bottom region were approximately 138° C. and 3.4 kg/cm$^2$, respectively.

Comparative Example 1

Figure 4:
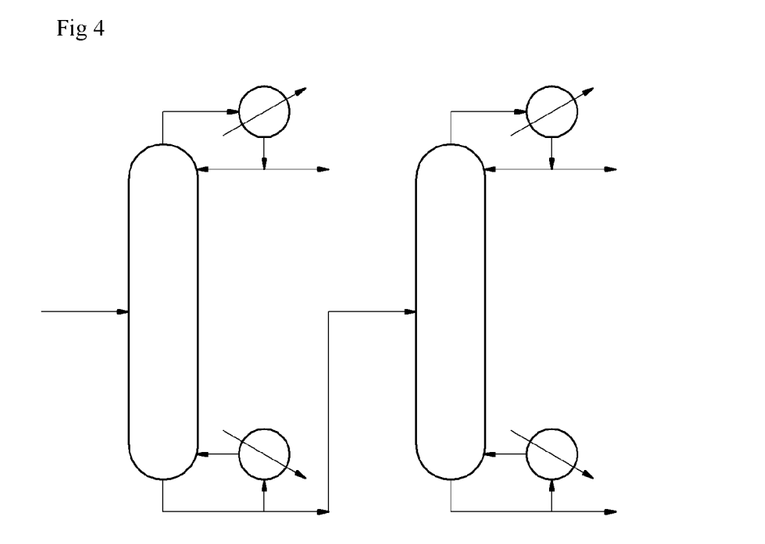
FIGS. 4 and 5 show a purification device according to a comparative example of the present invention.

A liquid feed including 98.6 wt % of IPA, approximately 3,000 ppm of water, and approximately 1.1 wt % of other impurities was purified in a purification device in which two general columns were connected without a dehydration process as shown in FIG. 4. In this case, top operating temperature and pressure of a first column were adjusted to approximately 76° C. and 1.12 kg/cm$^2$, respectively, and bottom operating temperature and pressure of the first column were adjusted to approximately 93° C. and 1.54 kg/cm$^2$, respectively. In addition, top operating temperature and pressure of the second column were adjusted to approximately 83° C. and 1.04 kg/cm$^2$, respectively, and bottom operating temperature and pressure of the second column were adjusted to approximately 110° C. and 1.18 kg/cm$^2$, respectively.

Comparative Example 2

Figure 5:
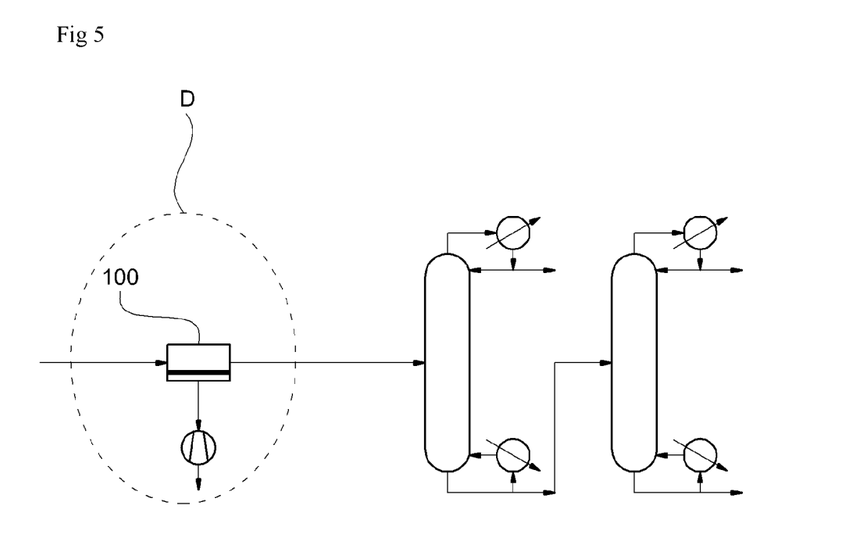

As shown in FIG. 5, a process was performed by the same method as described in Example 1, except that a feed passing through a membrane system was purified by being introduced into a purification device in which two general columns were connected, instead of a DWC. In this case, top operating temperature and pressure of a first column were adjusted to approximately 70° C. and 1.12 kg/cm$^2$, respectively, and bottom operating temperature and pressure of the first column were adjusted to approximately 93° C. and 1.54 kg/cm$^2$, respectively. In addition, top operating temperature and pressure of a second column were adjusted to approximately 83° C. and 1.04 kg/cm$^2$, respectively, and bottom operating temperature and pressure of the second column were adjusted to approximately 110° C. and 1.18 kg/cm$^2$, respectively.

Comparative Example 3

A process was performed by the same method as described in Example 1, except that a liquid feed including 98.6 wt % of IPA, approximately 3,000 ppm of water, and approximately 1.1 wt % of other impurities was introduced directly into a DWC shown in FIG. 2 without a dehydration process. In this case, a reflux ratio of a top region of the DWC was adjusted to 52, operating temperature and pressure of the top region were adjusted to approximately 78° C. and 1.12 kg/cm$^2$, respectively, and operating temperature and pressure of a bottom region were adjusted to approximately 111° C. and 1.37 kg/cm$^2$, respectively.

Comparative Example 4

Purification was performed by the same method as described in Example 1, except that a product including IPA was obtained from 35 plates of a DWC having the number of theoretical plates of 90 plates.

Comparative Example 5

Purification was performed by the same method as described in Example 1, except that a product including IPA was obtained from 85 plates of a DWC having the number of theoretical plates of 90 plates.

In this case, a content of a high boiling point component in IPA obtained from a lower product outflow region was detected at approximately 442 ppm.

Comparative Example 6

A process was performed by the same method as described in Example 1, except that a water content in a feed introduced into a purification means after a dehydration means was adjusted to approximately 1,500 ppm.

A total amount of energy and a water content in IPA used in Examples and Comparative Examples are summarized and listed in Tables 1 and 2.

TABLE 1

| | | Example 1 | Example 2 | Example 3 | Example 4 | Example 5 | Example 6 | Example 7 |
|---|---|---|---|---|---|---|---|---|
| Heat duty | Condenser | 1.9 | 1.86 | 1.81 | 1.9 | 1.9 | 1.88 | 2.16 |
| (Gcal/hr) | Reboiler | 1.88 | 1.84 | 1.8 | 1.88 | 1.88 | 1.84 | 2.27 |
| Saved amount of energy (Gcal/hr) | | 1.14 | 1.18 | 1.22 | 1.14 | 1.14 | 1.18 | 0.61 |

TABLE 1-continued

|  | Example 1 | Example 2 | Example 3 | Example 4 | Example 5 | Example 6 | Example 7 |
|---|---|---|---|---|---|---|---|
| Energy saving rate (%) | 38% | 39% | 40% | 38% | 38% | 39% | 25% |
| Water content in IPA (ppm) | 89 | 100 | 110 | 110 | 100 | 65 | 100 |

Saved amount of energy: Saved amount of energy compared to C. Example 1,
Energy saving rate: Energy saving rate compared to C. Example 1

TABLE 2

|  |  | C. Example 1 | C. Example 2 | C. Example 3 | C. Example 4 | C. Example 5 | C. Example 6 |
|---|---|---|---|---|---|---|---|
| Heat duty (Gcal/hr) | Condenser | 3.13 | 2.98 | 2.02 | 1.9 | 1.9 | 1.9 |
|  | Reboiler | 3.02 | 2.88 | 2 | 1.88 | 1.88 | 1.88 |
| Saved amount of energy (Gcal/hr) |  | 0 | 0.14 | 1.02 | 1.14 | 1.14 | 1.14 |
| Energy saving rate (%) |  | 0% | 5% | 34% | 38% | 38% | 38% |
| Water content in IPA (ppm) |  | 100 | 100 | 100 | 142 | 100 | 130 |

Saved amount of energy: Saved amount of energy compared to C. Example 1,
Energy saving rate: Energy saving rate compared to C. Example 1
* C. Example: Comparative Example

The invention claimed is:

1. A method for purifying isopropyl alcohol, comprising:
removing water by providing a feed including isopropyl alcohol and water to a membrane system to obtain a feed having a water content adjusted to 1,200 ppm or less; and performing purification by providing the feed having the water content adjusted to 1,200 ppm or less to a divided wall column to obtain a discharged product including purified isopropyl alcohol and having a water content of 150 ppm or less,
wherein the divided wall column is divided into a feed inflow region, a top region, a bottom region and a product outflow region, and the product outflow region is divided into an upper product outflow region and a lower product outflow region,
wherein the discharged product including the purified isopropyl alcohol and having a water content of 150 ppm or less is discharged from the lower product outflow region of the divided wall column, and
wherein the discharged product including the purified isopropyl alcohol and having a water content of 150 ppm or less is obtained at a location of 50 to 90% of plates among a number of theoretical plates calculated based on a top of the divided wall column.

2. The method according to claim 1, wherein the membrane system is a pervaporation system or a vapor permeation system.

3. The method according to claim 1, wherein the feed provided to the membrane system has a water content of 1,200 to 5,000 ppm.

4. The method according to claim 1, wherein the temperature of the top region of the divided wall column is adjusted to 40 to 120° C.

5. The method according to claim 1, wherein the pressure of the top region of the divided wall column is adjusted to 0.1 to 10.0 kg/cm$^2$.

6. The method according to claim 4, wherein the temperature of flow discharged from the lower product outflow region of the divided wall column is 60 to 130° C.

7. The method according to claim 5, wherein the pressure of the lower product outflow region of the divided wall column is 0.3 to 6.0 kg/cm$^2$.

8. The method according to claim 4, wherein the temperature of the bottom region of the divided wall column is 80 to 160° C.

9. The method according to claim 5, wherein the pressure of the bottom region of the divided wall column is 0.3 to 6.0 kg/cm$^2$.

* * * * *